United States Patent
De Smet

(10) Patent No.: US 7,545,998 B2
(45) Date of Patent: Jun. 9, 2009

(54) SYSTEM FOR MEASUREMENT AND DETECTION OF PARAMETERS AND ANOMALIES

(75) Inventor: Marie-Anne De Smet, Monbrun (FR)

(73) Assignee: Airbus France, Toulouse (FR)

( * ) Notice: Subject to any disclaimer, the term of this patent is extended or adjusted under 35 U.S.C. 154(b) by 0 days.

(21) Appl. No.: 11/752,969

(22) Filed: May 24, 2007

(65) Prior Publication Data

US 2008/0025664 A1    Jan. 31, 2008

(30) Foreign Application Priority Data

May 24, 2006   (FR)   ................................. 06 51904

(51) Int. Cl.
  *G02B 6/00*   (2006.01)
(52) U.S. Cl. ........................ 385/12; 52/309.9
(58) Field of Classification Search .................. 385/12, 385/37, 126; 250/227.12, 227.16, 227.23, 250/227.27; 356/478
  See application file for complete search history.

(56) References Cited

U.S. PATENT DOCUMENTS

| | | | |
|---|---|---|---|
| 4,581,527 A | 4/1986 | Crane et al. | |
| 4,901,584 A * | 2/1990 | Brunner et al. | 73/862.046 |
| 5,077,820 A * | 12/1991 | Tokuda et al. | 385/116 |
| 5,118,931 A * | 6/1992 | Udd et al. | 250/227.16 |
| 5,144,690 A * | 9/1992 | Domash | 385/12 |
| 5,374,821 A * | 12/1994 | Muhs et al. | 250/227.16 |
| 6,198,861 B1 | 3/2001 | Kellar et al. | |
| 6,370,964 B1 * | 4/2002 | Chang et al. | 73/862.046 |
| 6,564,640 B1 * | 5/2003 | Allaei | 73/583 |
| 6,639,681 B1 * | 10/2003 | Magne et al. | 356/478 |
| 6,640,647 B1 * | 11/2003 | Hong et al. | 73/800 |
| 6,765,194 B2 * | 7/2004 | Holz et al. | 250/227.12 |
| 7,050,716 B2 * | 5/2006 | Nakaya et al. | 396/548 |
| 2005/0061076 A1 * | 3/2005 | Kim | 73/587 |

FOREIGN PATENT DOCUMENTS

WO   WO 9953283 A1 *  10/1998

* cited by examiner

*Primary Examiner*—James P Hughes
*Assistant Examiner*—Peter Radkowski
(74) *Attorney, Agent, or Firm*—Perman & Green, LLP

(57) ABSTRACT

The subject of the invention is a system for measuring the state of panels in real time, particularly of one or more composite panels, characterized in that it has a network of very fine waveguides connected to a series of transducer sensors that are designed to send and receive signals in the waveguides, these sensors being themselves connected to a computer device such as a microprocessor device.

11 Claims, 2 Drawing Sheets

SYSTEM FOR MEASUREMENT AND DETECTION OF PARAMETERS AND ANOMALIES

FIELD

The disclosed embodiments concern a system for measuring and detecting parameters and anomalies adapted for measuring physical parameters of panels and notably panels for the fuselage or wing boxes of aircraft.

Within the scope of design and qualification, but also for use and maintenance of aircraft, it is necessary to be able to evaluate the stresses experienced by the structures, and to be able to determine whether these structures are damaged by the appearance of cracks or fissures or by the appearance of delaminations in the case of composite structures.

The disclosed embodiments are directed to the implementing of a means for monitoring the state of health of composite materials, their elaboration with the maintenance of the airplane, by passing through all the steps of their manufacture.

BACKGROUND

Currently there are visual monitoring means that are difficult to implement, or there are destructive monitoring means, but there are no means permitting following the state of structural panels of the aircraft in a non-destructive manner in real time throughout the life of the aircraft.

The disclosed embodiments seek to propose a system adapted to such tracking in real time that allows knowing the state of a constellation of properties that characterize the conformity of the panels relative to the technical specifications for different stages of the aircraft life.

The problems to be resolved for such a system are:
  during manufacturing, to have available a means for monitoring the state of health and for tracking the polymerization of the composite material. In fact, the manufacture of composite panels notably comprises a firing step that requires very precise conditions and cycles of temperature and duration. These conditions and these cycles may have deviations that are harmful to the homogeneous polymerization of the material, and the system must be adapted to detect stresses and/or hot points during the manufacture of the parts, instead of only using monitoring means after polymerization in the case when an alarm is given by the system.
  in maintenance, to have available a monitoring means permitting the tracking of panels and adapted for a predictive maintenance, yet remaining negligible in terms of mass and space required and only requiring a small electrical power to function.

SUMMARY

To do this, the disclosed embodiments provide a system for measuring the state of the panels in real time, particularly of one or more composite panels, comprising a network of very fine waveguides connected to a series of transducer sensors that are designed to send and receive signals in the waveguides, these sensors being themselves connected to a computer device such as a microprocessor device, the computer device thus carrying out a tracking and monitoring of the parameters measured by the sensors.

The waveguides are advantageously optical fibers and the signals are optical signals, the transducers being in this case optoelectronic transducers.

The system network according to the invention is designed to remain operational even if it is partially damaged. To do this, the distance between waveguides is set to a value of less than the minimum dimensions of the defects to be detected.

The connection of the network to a computer device permits an automatic analysis and diagnosis.

Advantageously, the distance between waveguides is set to a value of less than the minimum defects to be detected.

According to one preferential embodiment, the network is organized in a line-column matrix, the sensors being arranged both at the end of the line waveguides and of the column waveguides.

Advantageously, the computer device has a memory containing a map of a field of nominal parameters for the panel or panels, means for calculating measurements from the data sent by the transducer sensors, means for comparison of said measurements with the nominal parameters, alarm means and/or means for storing abnormal values and means for transmitting the values measured.

According to a particular embodiment of the invention, the waveguides are optical fibers, the signals are optical signals, and for which the transducer sensors are optoelectronic transmitter-receivers.

Advantageously, the transducers send optical signals that can be modulated according to the characteristics of the parameters or defects to be detected.

More particularly, the optical signals are calibrated to provide a response representative of the temperature of the fibers and the medium through which they pass.

Advantageously, the waveguide network is created in a sheet incorporated in a composite panel during its manufacture.

According to a first mode, the sheet is positioned under a first layer of skin of the composite panel.

According to an alternative mode, the sheet constitutes an internal layer of the composite panel.

The sensors are preferably arranged in a line at the periphery of the panel, and the waveguides are advantageously of microscopic diameter.

According to particular embodiments of the system according to the invention, the waveguides have fibers provided with a permeable covering so that the evanescent field generated by reflections in the fibers interacts with the medium through which they pass and/or the material of the sheet, and/or the material of the coverings of the waveguides is a conductor of electricity.

BRIEF DESCRIPTION OF THE DRAWINGS

Other characteristics and advantages of the invention will be better understood upon reading the description that follows of one non-limiting example of embodiment of the invention in reference to the attached drawings, which show.

DETAILED DESCRIPTION

Figure 1:
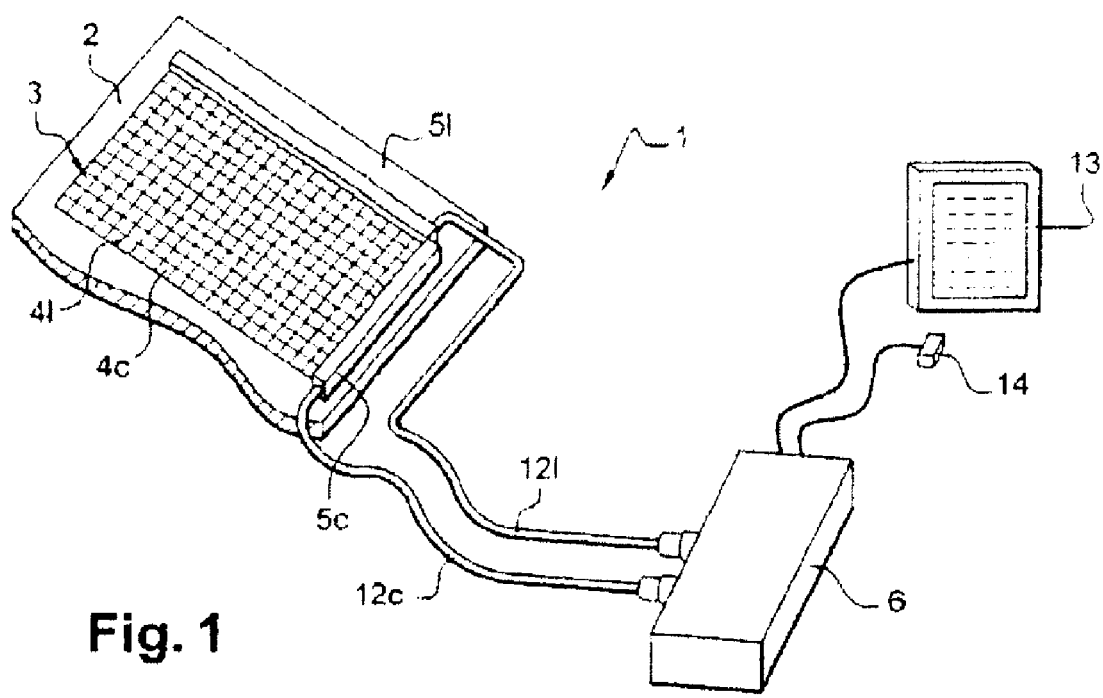
in FIG. 1: a schematic representation of a system according to the invention.

The system 1 for measuring the state of panels in real time represented in FIG. 1 comprises a waveguide network 3 made up of very fine optical fibers 4*l*, 4*c*, or even fibers 4*l*, 4*c* of microscopic diameter of the order of microns, connected to a series of optoelectronic transducer sensors 5*l*, 5*c*.

The transducer sensors are configured to send a beam of light and to receive this beam after reflection on the end of the fiber opposite to the end of the fiber provided with the sensor.

The sensors are themselves connected to a computer device 6 such as a microprocessor device, by cables 12*l*, 12*c*, 12*lc* or by a wireless connection, for example a radio frequency device.

Figure 3:
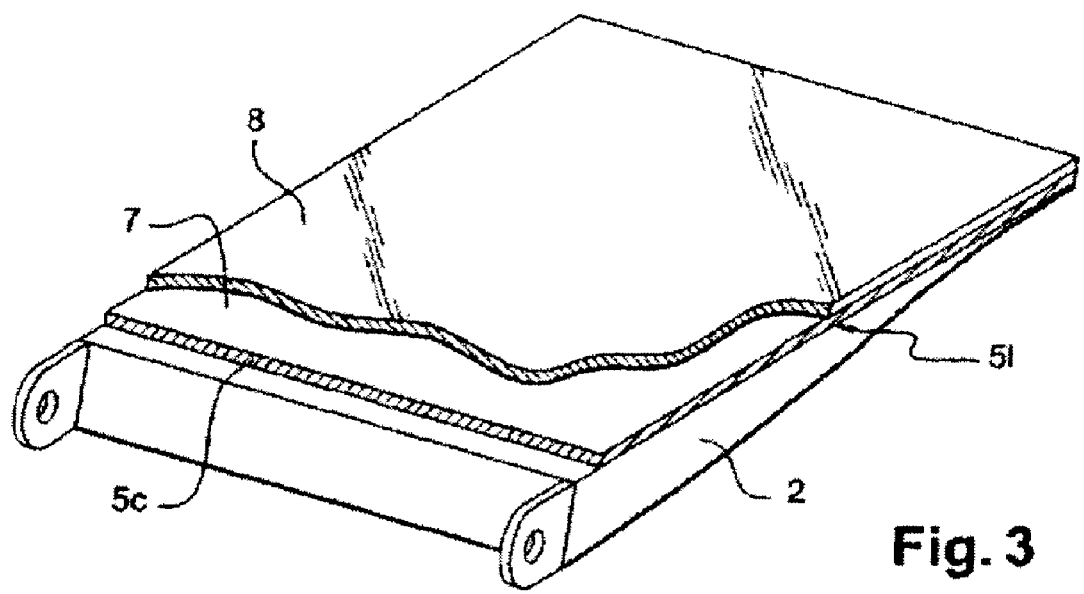
in FIG. 3: a schematic representation of a panel equipped with the network of FIG. 2.

The system of FIG. 1 is notably designed to monitor the behavior of one or more composite panels 2 of the aircraft structure such as shown in FIG. 3 or in which the network is integrated.

Figure 2:
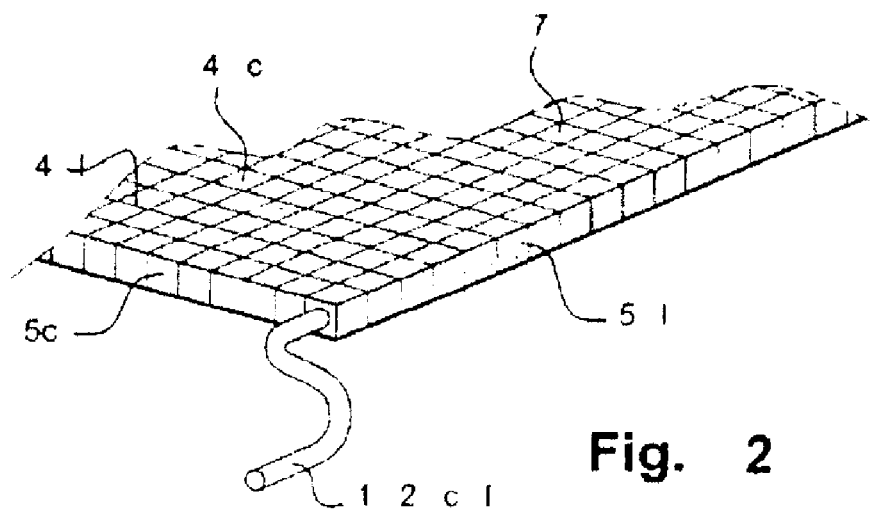
in FIG. 2: a schematic representation of a fiber network of the system of FIG. 1.

The network is shown in FIG. 2. This network is organized in a line and column matrix l, c and has a succession of line fibers 4*l* as well as a succession of column fibers 4*c*.

Sensors 5*l*, 5*c* are arranged at the end of line fibers 4*l* and column fibers 4*c* so that a defect in the panel structure can be localized as a function of the line and column of the fibers detecting it.

The network of fibers shown in FIG. 2 is made on a sheet 7 forming a substrate on which the fibers are arranged.

Advantageously, sheet 7 is incorporated in composite panel 2 during its manufacture and, either the sheet is positioned on the surface of the panel and its thickness remains negligible compared to that of the panel so that the sheet does not change the characteristics of the panel, or the sheet is positioned under a first layer 8 of the skin of composite panel 2 and the fiber network possibly participates in the structural strength of the panel, or, finally, the sheet constitutes an internal layer 17 of composite panel 2 and becomes a constituent of said panel, the fiber network thus behaving as a reinforcement lattice of the panel.

Figure 4A:
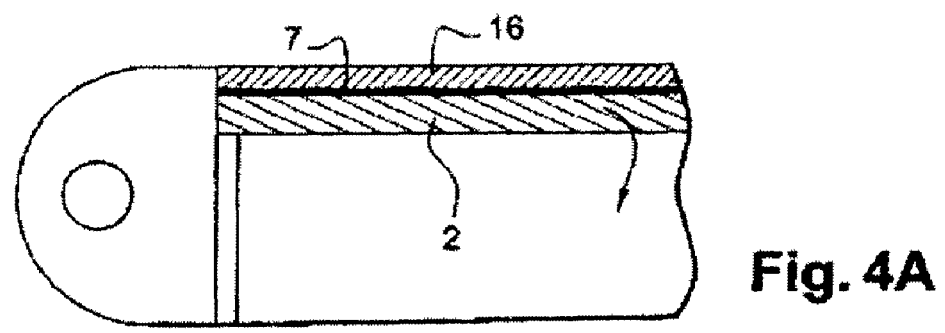
in FIG. 4A, a view of a detail in side section of the panel of FIG. 3.
Figure 4B:
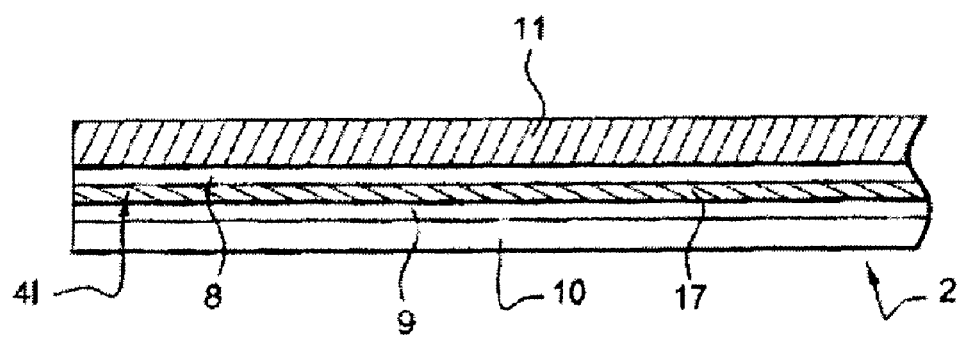
in FIG. 4B: a schematic sectional view of one alternative embodiment of the panel of FIG. 3.

FIG. 4A corresponds to the embodiment in which the sheet is positioned at the surface of the panel under a layer of paint 16 and FIG. 4B to the embodiment in which the sheet is a structural layer 17 positioned in the panel under a first layer 11 and a second layer 8 of panel 2 and above lower layers 9 and 10.

In every case and as shown in FIG. 3, sensors 5*l*, 5*c* are arranged in a line at the periphery of the panel, on both sides of the panel according to the example.

In order to precisely localize defects, the distance between the fibers is set at a value of less than the minimum dimensions of the defects to be detected.

For example, in the case of a network designed to detect delaminations of the panel on a surface of the order of $mm^2$, the fibers are arranged according to a distance of less than a half-millimeter so that discrimination of the position of the defects is possible and so that, in the case of localized damage to the network, the fibers situated around the damaged zone can always permit monitoring the zones closest to the defect, and [to indicate that] the surface of the panel still under surveillance remains compatible with predetermined surveillance criteria.

Within the scope of automating measurements or monitoring in real time, computer device 6 has a memory containing a cartographic representation or a map of a field of nominal parameters of the panel or panels.

This map can notably comprise parameters such as a matrix of minimum-maximum values that are not to be surpassed for local stresses, temperature, infiltration of water or another parameter whose monitoring is required during manufacture of the panel, during testing or during normal functioning of the aircraft.

This cartographic representation constitutes a predefined comparison model with regard to the behavior of the zone covered by the network.

The comparison model defines a map of the field of parameters that one wishes to monitor during manufacture, assembly or maintenance.

During manufacture, the model can represent the tracking of the polymerization of the composite panel, the detection of delaminations, levels of porosity or other parameters representing a good fabrication of the panel.

Thus, the computer notably provides a map of significant signals for parameters that must be analyzed as a function of the stage of advancement of the composite making up the panel.

For panel maintenance, the model can be adapted to detect delaminations, infiltrations of liquids into the skin, or a degradation of the panel by too great an increase in temperature or by mechanical stresses that are too large.

The model is also designed so that it permits making an auto-verification of the proper functioning of the sensor elements.

The computer also has means for calculating measurement data from data sent by sensor transducers 5*l*, 5*c* in order to translate the values measured into values representative of the local and global stresses of the panel.

It also has means for comparing said measurements with nominal parameters and can have alarm means 13 such as a display screen or sound and/or visual indicators to give an indication in real time of the panel load or to display the stress parameters to which the panel is subjected.

These real-time alarm means can notably be used to adapt the firing of the panel during its manufacture.

Integrated analysis can be done, in particular, with regard to thresholds. When a threshold is surpassed, the computer registers an alarm that is either displayed or declared during a final inspection.

For its use throughout the life of the aircraft, the computer also has means for storing abnormal values and means 14 for transmitting these measured values in order to unload measurements that have been made over a period of use, to an external diagnostic system during the maintenance phase following this period of use.

Within the scope of a surveillance of several types of stress, e.g., mechanical, thermal, as well as water infiltration, the transducer sensors of the measurement system according to the invention are optoelectronic transmitter-receivers 5*l*, 5*c* sending optical signals that can be modulated according to the characteristics of the defects to be detected. For example, the signals can be pulses to measure the propagation time of the optical signal in the case of measurements of mechanical stresses or a particular wavelength for which propagation defects will permit determining the local temperature of the panel. In this latter case, the optical signals are calibrated to provide a response representative of the temperature of the fibers and the medium through which they pass.

Moreover, in order to permit measuring the infiltration of water into the panel, fibers 4*l*, 4*c*, preferably arranged in a deep layer of the panel, are provided with a permeable covering so that the evanescent field, which is generated by reflections in the fibers, interacts with the medium that the fibers pass through, and is influenced by the proportion of water in the panel.

The system according to the invention is better performing than other non-destructive monitoring means since it is positioned in the core of the material and it permits detecting anomalies of elaboration, of manufacture, as well as the beginning of damage, well before a critical threshold.

This system permits reducing manufacturing and maintenance time and cost since it is no longer necessary to conduct an inspection as long as the threshold to be detected has not been reached.

According to a particularly advantageous embodiment suitable for the outer panels of an aircraft, the material of the sheet and/or the material of the fiber coatings is electrically conductive so as to serve as a lightning guide.

The network can be manufactured according to organic-inorganic hybrid material techniques of UV lithography by using a very photosensitive material that can be deposited over thicknesses from several dozen nanometers to several hundred microns.

The invention has been presented within the scope of fabricating composite panels for aircraft structures, but can be used in other industrial sectors, such as the automotive, railway and shipbuilding or nuclear construction sectors; likewise, the example described has optical fibers; however, the invention is not limited to these fibers, but is applicable to waveguides.

The invention claimed is:

1. A system for measuring the state of one or more composite panels in real time comprising:
    a network of very fine waveguides fabricated in a sheet incorporated in a composite panel during its manufacture and connected to a series of transducer sensors that are designed to send and receive signals in the waveguides,
    these sensors being themselves connected to a computer device such as a microprocessor device,
    wherein the network is organized into a line-column matrix, and the sensors are arranged at the end of line waveguides and column waveguides, and wherein
    the waveguides are optic fibers provided with a permeable covering so that the evanescent field which is generated by the reflections in the fibers interacts with the medium through which they pass.

2. The measurement system according to claim 1 for which the distance between waveguides is set at a value of less than the minimum dimensions of defects to be detected.

3. The measurement system according to claim 1 for which computer device has a memory containing a cartographic representation or a map of a field of nominal parameters for the panel or panels, means for calculating measurements from the data sent by transducer sensors, means for comparing said measurements with the nominal parameters, alarm means and/or means for storage of abnormal values and means for transmission of the values measured.

4. The measurement system according to claim 1 for which the waveguides are optical fibers, the signals are optical signals and for which the transducer sensors are optoelectronic transmitter-receivers.

5. The measurement system according to claim 4 for which the transducers send optical signals that can be modulated according to the characteristics of the parameters or defects to be detected.

6. The measurement system according to claim 5 for which the optical signals are calibrated to provide a response representative of the temperature of the fibers and of the medium through which they pass.

7. The measurement system according to claim 1 for which the sheet is positioned under a first layer of skin of composite panel.

8. The measurement system according to claim 1 for which the sheet constitutes an internal layer of composite panel.

9. The measurement system according to claim 1 for which sensors are arranged in a line at the periphery of the panel.

10. The measurement system according to claim 1 for which waveguides are of microscopic diameter.

11. The measurement system according to claim 1 for which the material of the sheet and/or the material of the waveguide coverings is electrically conductive.

* * * * *